United States Patent [19]
Maxfield et al.

[11] Patent Number: 5,514,956
[45] Date of Patent: May 7, 1996

[54] RELEASE MECHANISM FOR HIGH-MAGNETIZATION MAGNETIC INSPECTION APPARATUS FOR USE IN INSPECTING STORAGE TANK BOTTOMS

[75] Inventors: Bruce W. Maxfield, Oakland; Pamela C. Fitzgerald, Berkeley, both of Calif.

[73] Assignee: Industrial Sensors and Actuators, San Leandro, Calif.

[21] Appl. No.: 320,326

[22] Filed: Oct. 11, 1994

[51] Int. Cl.$^6$ .................................................. G01N 27/83
[52] U.S. Cl. .......................... 324/262; 324/228; 324/235; 324/242
[58] Field of Search .................................. 324/214–218, 324/226, 228, 235, 240–242, 262

[56] References Cited

U.S. PATENT DOCUMENTS

| | | | |
|---|---|---|---|
| 1,899,525 | 2/1933 | Perry et al. | 324/262 |
| 2,313,729 | 3/1943 | Barnes | 324/262 X |
| 4,041,379 | 8/1977 | Karlsson | 324/262 X |
| 4,258,319 | 3/1981 | Shimada et al. | 324/262 X |
| 4,314,203 | 2/1982 | Haberlein | 324/262 |
| 4,510,447 | 4/1985 | Moyer | 324/262 X |
| 4,634,976 | 1/1987 | Tiitto | 324/262 X |
| 4,814,705 | 3/1989 | Saunderson | 324/225 |

OTHER PUBLICATIONS

Wiegant, "Automated NDT of Storage Tank Bottoms," Contribution to the KINT—BANT Symposium, Sep. 8–9, 1988, Antwerp, Belgium.

*Primary Examiner*—Gerard R. Strecker
*Attorney, Agent, or Firm*—Elliot B. Aronson

[57] ABSTRACT

Tank bottom inspection apparatus of the magnetic flux leakage type having a powered release mechanism for reducing the magnetic attraction of the apparatus to the tank bottom. The apparatus is wheeled over the tank bottom surface and includes a magnet assembly disposed over the surface for inducing magnetic flux in the material under inspection and a sensor assembly for detecting magnetic flux leakage from the material indicative of magnetic anomalies. A powered actuator permits the operator to retract the magnet assembly away from the surface, reducing the magnetic attraction to the surface and thereby reducing magnetic resistance to movement of the apparatus over the surface. The operator retracts the magnet assembly for maneuvering the apparatus over and around obstacles on the surface with greatly reduced magnetic attraction to the surface. The operator is then able to return the magnet assembly to a precise inspection position for continued inspection of the surface. In one embodiment an actuator is coupled to the magnet assembly so as to move the magnet assembly relative to the apparatus wheels, which remain in contact with the surface. In another embodiment the actuator may be extended to raise the front of the apparatus, including the front wheels, off the surface so as to displace the magnet assembly away from the surface, thereby providing enhanced maneuverability for avoiding obstacles and for positioning the apparatus for inspection of the surface.

7 Claims, 4 Drawing Sheets

RELEASE MECHANISM FOR HIGH-MAGNETIZATION MAGNETIC INSPECTION APPARATUS FOR USE IN INSPECTING STORAGE TANK BOTTOMS

BACKGROUND OF THE INVENTION

The present invention relates generally to apparatus for the detection and measurement of magnetic anomalies in magnetic materials and is more particularly directed to manually operated apparatus for detecting magnetic flux leakage such as used for inspecting for defects in the bottoms of chemical and petroleum storage tanks.

Chemical and petroleum storage tanks face gradual and continual deterioration due to the harsh chemical environment both outside and within the vessel. The steel walls of a tank are subject to corrosion, pitting, and other chemical and physical processes that can cause localized damage to the walls. Such localized damaged regions can develop into leaks or in extreme cases can lead to rupture of the tank. The tank bottom is exposed to corrosion or similar damage from the underside as well as from the top side. A tank typically rests on sand, gravel, crushed limestone, clay or similar base of varied composition. When the tank is filled, the bottom flexes and presses into the material under the weight of the contents. When the tank is then emptied, the bottom rises causing air and moisture to be drawn in, which accelerates the underside deterioration process.

To guard against environmentally damaging leaks or other tank failure, tank bottoms should be inspected periodically for early signs of damage conditions that may result in leakage. The underside of the tank bottom of course is inaccessible and thus cannot be inspected directly. One popular form of inspection apparatus looks for magnetic anomalies caused by local damage to the steel tank bottom. This apparatus includes one or more strong permanent magnets or electromagnets that induce a magnetic field within the steel plate forming the tank bottom that in effect locally magnetizes the plate. A region of the plate without defects produces an induced magnetic field of known form that is generally confined within the plate. Localized defects from corrosion, pitting and the like cause this generally confined magnetic flux to "leak out" of the steel plate where it may be detected by the inspection apparatus positioned just above the plate surface, even if the defect producing the magnetic anomaly is on the inaccessible underside of the plate. Thus, detecting a magnetic anomaly may signal the site of a defect in the steel bottom.

For good inspection sensitivity and accuracy with respect to corrosive type defects, it is desirable to apply the largest possible magnetizing force to the material. There is a practical limitation, however, to the magnitude of the largest magnetizing force that can be applied: The attractive magnetic force between the magnets in the apparatus and the material being magnetized can become unmanageably large. If the apparatus is to be usable, it must strike a balance between the magnitude of the magnetization induced in the material under inspection—a larger induced magnetization provides greater sensitivity to magnetic anomalies—and the strength of the magnetic attraction between this material and the apparatus—a larger magnetic attraction hinders maneuverability of the apparatus.

Typical magnetic inspection apparatus includes a carriage mounted on wheels that carries the magnet for inducing the field within the tank bottom, the sensors for detecting the flux leakage, a motor for driving the wheels, and various other subassemblies needed for the apparatus to function. To perform an inspection, the apparatus is wheeled slowly across the tank bottom while the on-board sensors search a strip, typically about twelve inches wide, for magnetic leakage flux. The apparatus is manually maneuvered over the tank bottom in this way until the entire bottom is covered.

The magnetic inspection apparatus is generally difficult to manipulate. The apparatus is heavy, typically weighing 100 to 300 pounds (44 to 130 kilograms). The necessarily strong magnetic attraction between the on-board magnet and the steel plate of the tank bottom adds substantially to the difficulty of freely moving the apparatus over the surface. Even with the on-board drive motor for the wheels, manipulating the apparatus in the course of inspecting a full tank bottom can be a laborious operation. A storage tank having an 80 foot (25 m) diameter, for example, may take up to eight hours to inspect.

Maneuvering the apparatus is laborious in part because the operator must first "break" the attractive magnetic force whenever it is desired to re-position the apparatus for inspecting a new region of the plate, for example when a sidewall is reached, or to navigate the apparatus around or over obstacles such as plate welds. Steel plate on the order of ¼ to ½-inch thick (6 to 12 millimeters) is commonly welded to the tank bottom to patch previously discovered damage. When the edge of such patchwork is encountered, the operator must manually urge the apparatus over or around the welded edge to continue the inspection. Operators commonly find it burdensome to manipulate the apparatus back and forth over the tank bottom when the total attractive force exceeds about 200 pounds (about 90 kilograms) and extremely difficult if not prohibitively exhausting when the attractive force exceeds about 700 pounds (about 300 kilograms). At least one supplier has attempted to alleviate the burden on the operator by providing a foot pedal linked to the magnet assembly so that the operator may first displace the magnet away from the surface by depressing the foot pedal to break the magnetic attraction. In practice, however, the foot pedal still leads to operator fatigue over the course of several hours of inspection. Consequently, operator fatigue still places a practical limitation on the maximum magnetization that may be utilized, which in turn limits the sensitivity, accuracy and overall utility of the inspection apparatus.

SUMMARY OF THE INVENTION

The present invention provides a tank bottom inspection apparatus of the magnetic flux leakage type having a powered release mechanism for reducing the magnetic attraction of the apparatus to the tank bottom on command from the operator and greatly enhancing the maneuverability of the apparatus.

Briefly, the present invention provides magnetic flux leakage inspection apparatus including a magnet assembly with one or more magnets disposed in a predetermined inspection position over the surface to be inspected for inducing magnetic flux in the material under inspection; a sensor assembly for detecting magnetic flux leakage from the material indicative of magnetic anomalies in the material; and a plurality of wheels, or similar supports facilitating movement, on which the apparatus is mounted to permit an operator to maneuver the apparatus over a substantially planar surface for inspection thereof. To this apparatus is added at least one actuator for moving the magnet assembly between the inspection position and a retracted position, in which the magnet assembly provides a reduced magnetic attraction to the surface so as to reduce magnetic resistance to movement of the apparatus over the surface. A source of power is coupled to the actuator and is operable on command from the operator for bringing about powered movement of the magnet assembly between the inspection position and the retracted position, whereby the operator is able to move the magnet assembly to the retracted position, even in the presence of a strong magnetic attraction, for maneuvering the apparatus over and around obstacles on the surface with greatly reduced magnetic attraction to the surface and is then able to return the magnet assembly to the inspection position for continued inspection of the surface.

In one embodiment an actuator is coupled to said magnet so as to move the magnet relative to the apparatus wheels or similar supports, which remain in contact with the surface in both the inspection position and the retracted position of the magnet. Where the magnet and sensor assembly are mounted together in a scan bar assembly, the actuator may move the whole scan bar assembly generally perpendicular to the surface as the wheels remain on the surface.

In another embodiment the actuator is disposed on the apparatus so that activation of actuator when the magnet is in its inspection position urges one or more of the wheels off the surface. This in turn retracts the magnet farther from the surface so as to reduce the strength of the magnetic attraction. For example, in this embodiment the actuator may be mounted at the front of the inspection apparatus and include an extensible actuator rod formed at one end for engagement with the surface under inspection. Extension of the rod raises the front of the apparatus, and in particular the front wheels, off the surface. In this position the apparatus is supported by its rear wheels or similar rear supports and by the actuator, which is in contact with the surface at the end formed for that purpose. The magnet assembly in this position is necessarily displaced away from the surface, and hence the magnetic attraction to the surface is reduced. With this three-point support and consequent reduced magnetic attraction, the apparatus may be maneuvered more readily over the surface. The engagement end of the actuator in this embodiment may be provided with a ball castor providing for reduced sliding or rolling friction with the surface as the rear wheels or similar rear supports turn and hence providing for greater maneuverability.

Apparatus according to the invention provides a number of advantages. It provides greater maneuverability of the heavy apparatus. It enables larger attractive magnetic forces to be used than those typically found in prior art apparatus. The larger applied magnetic forces produce a larger volume or magnitude of induced magnetization in the material under inspection, and this tends to yield larger signals, which are less influenced by external noise sources (such as nearby machine tools or arc welding apparatus often used for repairs to tank bottoms) and are less influenced by temperature variations than are inspection apparatus of the prior art. The result is superior performance on thicker material and more accurate inspection. The invention enables substantially larger magnetic forces to be utilized than a human operator could otherwise manage. Because of the greater maneuverability and greater accuracy, the invention enables a tank bottom to be inspected faster and more economically. Even with large values of applied magnetic force and/or material magnetization, these advantages are achieved with less manual labor by the operator, which greatly reduces the incidence of operator fatigue.

Other aspects, advantages, and novel features of the invention are described below or will be readily apparent to those skilled in the art from the following specifications and drawings of illustrative embodiments.

DETAILED DESCRIPTION OF ILLUSTRATIVE EMBODIMENTS

Figure 1:
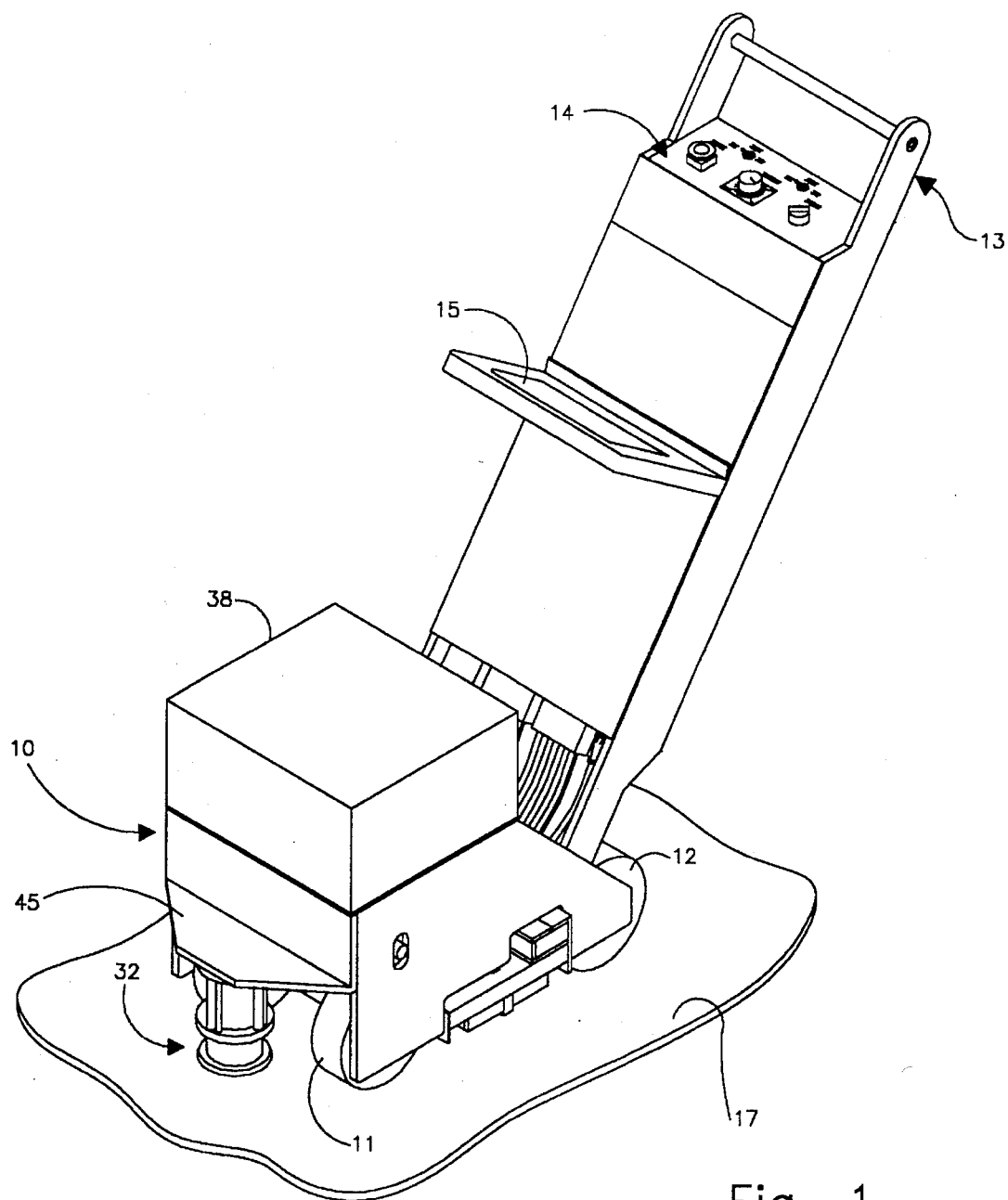
FIG. 1 is a perspective view of a magnetic inspection apparatus according to the invention.

An overall view of magnetic flux leakage inspection apparatus embodying the invention is shown in FIG. 1. The apparatus includes a carriage assembly 10 mounted on wheels 11 and 12 and a handle portion 13 by which an operator steers and manipulates the apparatus. Although wheels rotating about an axis are illustrated here, it will be appreciated by those skilled in the art that other support mechanisms can obviously be substituted for wheels, and the term "wheels" as used herein is intended to include all such mechanisms. Mounted on handle portion 13 are control panel 14 for controlling the electronic and motorized or other powered operation of the apparatus and display screen 15 for displaying inspection results and instructions and for generally communicating with the operator. The apparatus is shown positioned on a portion of a plate 17, which is under inspection. Plate 17 is of course composed of a magnetizable material and for storage tank bottoms will generally be a ferromagnetic steel plate.

Carriage assembly 10 includes a scan bar assembly 18 (see FIGS. 2 and 3) that includes a plurality of magnets 19 for inducing magnetization of plate 17 under inspection. The magnet configuration illustrated here provides two rows of permanent magnets 19 forming rows of north and south pole faces 20 and 21, respectively. The individual magnets 19 are magnetically coupled to one another through backing iron 22. When the pole faces of magnets 19 are magnetically coupled to plate 17, a continuous magnetic circuit is formed. Positioned between the poles 20 and 21 and forming a part of scan bar assembly 18 is a magnetic sensor assembly 24, which is used to detect magnetic leakage flux indicative of underlying magnetic anomalies associated with corrosive pitting and other plate damage. Other scan bar configurations of permanent magnets and electromagnets for providing the induced magnetization in the sample under inspection and other magnetic sensor assemblies for detecting the leakage flux are known and may also be used with the present invention, which is not intended to be limited to the specific configuration illustrated here.

Figure 2:
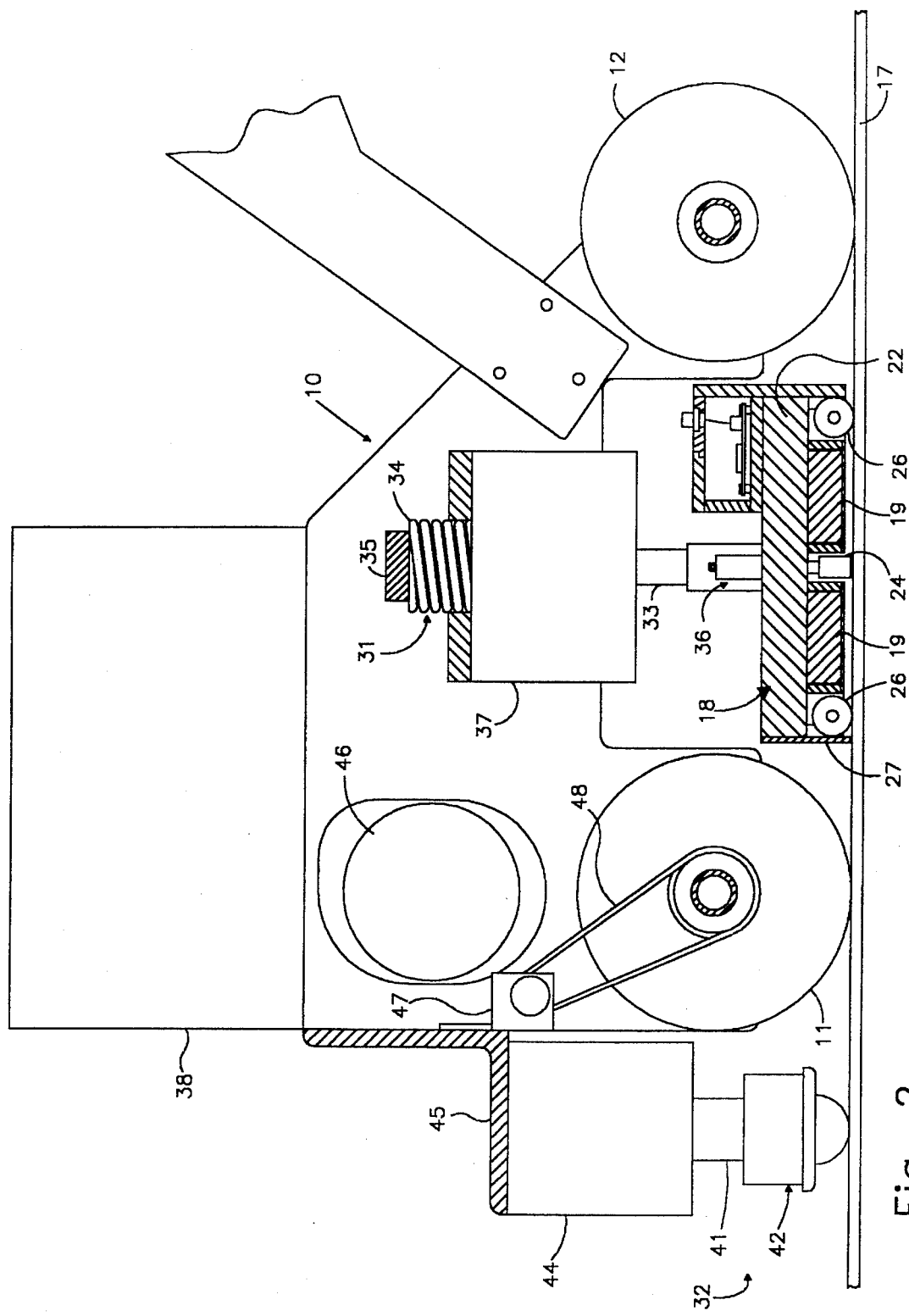
FIG. 2 is a side elevational view, partly in section, of the lower portion of the apparatus of FIG. 1.

For good measurement reliability it is important that the magnet pole faces 20 and 21 and the active sensor surface be disposed in an inspection position having a fixed distance from the surface of the plate under inspection. The magnitude of the magnetization induced in the plate under inspection, and the magnitude of any consequent flux leakage due to an anomaly, depends on the separation of the pole faces 20 and 21 from the surface of plate 17, and quantitative interpretation of measurement results depends on the positioning of magnetic probes 24 in the leakage flux. In the illustrated embodiment the scan bar assembly is mounted on roller bearings 26, which are mechanically secured in fixed relation to backing iron 22. Roller bearings 26 permit scan bar assembly 18 to roll over plate 17 independently of the mechanism supporting carriage assembly 10 on wheels 11 and 12. As seen in FIG. 2, in inspection position the active surface of sensor assembly 24 rides near plate 17 and is protected from collisions with protrusions in the plate surface by forward crash plate 27. The pole faces of magnets 19 are only slightly removed from the surface of plate 17.

Figure 3:
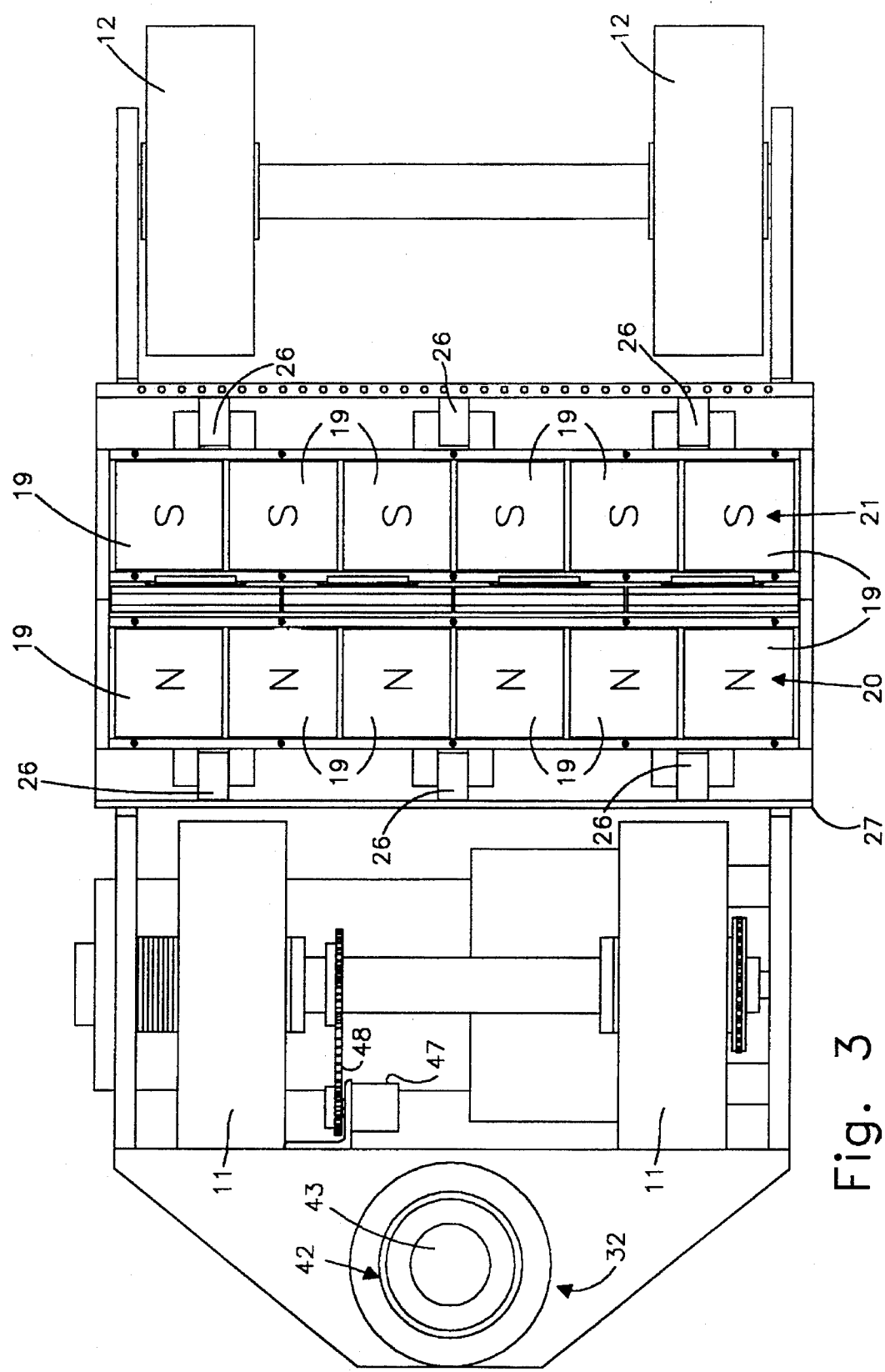
FIG. 3 is a bottom plan view of the apparatus of FIGS. 1 and 2.
Figure 4:
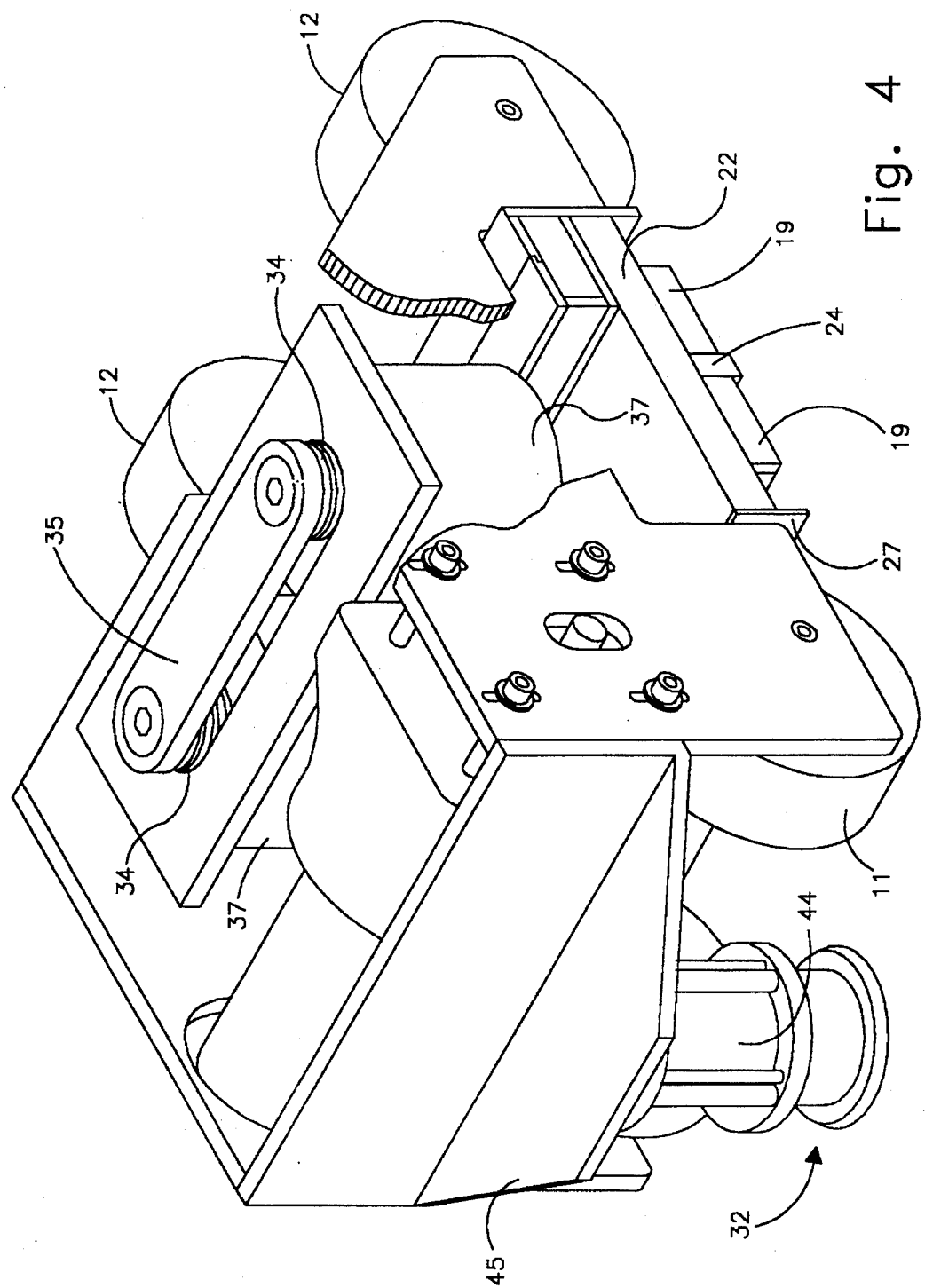
FIG. 4 is a perspective view, partially cut away, of a carriage assembly of the inspection apparatus of FIGS. 2 and 3.

To facilitate manipulation of the apparatus over and around obstacles and re-positioning in new directions, the embodiment of FIGS. 2–4 includes a pair of actuators 31 for raising and lowering scan bar assembly 18 with respect to carriage assembly 10 and ball castor actuator 32 for raising and lowering the carriage assembly as a whole. The actuators 31 and 32 serve to move magnets 19 to a retracted position farther removed from the surface of plate 17, and in addition ball castor actuator 32 serves to enhance the turning maneuverability of the apparatus, as explained more fully below. Actuators 31 are each provided by a pneumatic cylinder including cylinder rod 33, cylinder spring 34, and cylinder spring securement bar 35. The cylinder rods 33 are secured at one end to backing iron 22 by a bracket 36. Cylinder rod 33 is powered by air cylinder 37 rigidly attached to carriage assembly 10, which in turn is charged by air compressor 38. The air compressor of course need not be mounted on-board the inspection apparatus as shown in FIG. 2, but may alternatively be maintained separately and connected to the inspection apparatus by an air hose. For safety cylinder springs 34 are biased so that when air is released from cylinder 37, the springs force the scan bar assembly to return to its raised (retracted) position. The side-by-side actuators 31 provide for uniform retraction and extension of the scan bar assembly carrying magnets 19. Other actuator configurations may of course also be employed and may be preferred with other scan bar geometries. In particular, direct drive electric motors coupled to appropriate actuator mechanisms may alternatively be used in place of air-driven actuators 31 and air cylinders 37.

Ball castor actuator 32 includes cylinder rod 41 which is provided at one end with a ball castor assembly 42 including ball castor 43 for engaging the surface of plate 17. Actuator 32 together with air cylinder 44 are rigidly mounted at the front portion of carriage assembly 10 by mounting bracket 45. Cylinder rod 41 serves as a support member for at least partially supporting the weight of the inspection apparatus and the, albeit reduced, magnetic attraction forces. Actuators 31 and 32 and their associated air cylinders 37 and 44 are activated from control panel 14. The structure and operation of air actuators and cylinders and their control mechanisms are well known to those skilled in the art and need not be described in further detail here.

In operation, to inspect a strip of a tank bottom, the operator directs the apparatus in a straight line over the strip. Wheels 11 and 12 are normally mounted to rotate only around their central axes and so maintain the movement of the apparatus in a generally straight line. Scan bar assembly 18 is in its lowered position for inspection, bringing magnets 19 close to the surface of the plate 17 under inspection. The magnetic attraction between magnets 19 and plate 17 is generally quite strong. To maintain the movement against the resistive force of this magnetic attraction, front wheels 11 are driven by motor 46. The precise location of the apparatus as it moves in a straight line along the strip, which of course is needed so that detected defects may be found on the tank bottom, is recorded by counter 47 driven by band 48 coupled to the axle of one of the driven wheels. When an obstacle such as a plate weld is reached, the operator commands the actuators 31 from control panel 14 to retract. The powered actuators raise the scan bar assembly so that sensor assembly 24 is raised above the level of the plate weld or other obstruction. In addition to avoiding the weld, raising the scan bar assembly increases the distance between magnets 19 and plate 17, which causes a significant reduction in the strength of the magnetic attraction to the plate. This makes it considerably easier for the operator to maneuver the apparatus over or around an obstacle. To avoid the typical plate weld in petroleum storage tank bottoms, cylinder rod 33 should have a stroke on the order of 1.5 inches (4 cm).

When greater maneuverability out of a straight line is desired, such as when reaching a sidewall of the storage tank, front ball castor actuator 32 is used. In inspection position cylinder rod 41 is normally retracted in a resting position so that ball castor 43 is raised off of plate 17. On command from control panel 14 cylinder rod 41 is extended, bringing ball castor assembly 42 in engagement with plate 17 and raising the front end of carriage assembly 10 off the plate. This action moves the scan bar assembly together with magnets 19 away from the plate, significantly reducing the magnetic attraction. The apparatus is now supported on its two rear wheels 12 and on front cylinder rod 41 and ball castor 43. As the apparatus is now turned, the rear wheels turn and ball castor 43 readily glides over plate 17. The apparatus is able to be turned manually appreciably easier because the magnetic attraction to plate 17 has been greatly reduced and because the front wheels do not participate in the movement. When the front and rear wheels 11 and 12 are all in contact with the plate and rotate together, they constrain the apparatus to travel in a generally straight line, and that constraint is lifted when actuator 32 is extended.

The above descriptions and drawings disclose illustrative embodiments of the invention. Given the benefit of this disclosure, those skilled in the art will appreciate that various modifications, alternate constructions, and equivalents may also be employed to achieve the advantages of the invention. For example, other configurations and other types of actuators may be used, and the actuators may be linked to the scan bar assembly or carriage assembly through other types of couplings. In some circumstances, for example, it may be desirable to employ three ball castor actuators, one in front and two in the rear, instead of the one actuator 32 illustrated here. The three ball castors could be fixed, that is, not actuated, with actuation being performed as described, or alternatively the three ball castors could themselves be air-actuated for raising and lowering the scan bar assembly or the magnets directly. In addition, the apparatus may be configured with electric motors instead of air actuators. For example, a high-pitch screw actuator may be driven by a high-torque motor for lifting the scan bar assembly or for extending the ball castor 43. While air actuators are generally desirable because they can be made to extend and retract fairly rapidly even in the presence of strong magnetic attractions, electric motor driven mechanisms may nevertheless be desirable for battery-operated apparatus or other applications benefitting from the use of electric motors. Therefore, the invention is not to be limited to the above description and illustrations, but is defined by the appended claims.

What is claimed is:

1. Magnetic flux leakage inspection apparatus for inspecting a substantially planar surface of a magnetizable material for magnetic anomalies, said apparatus including a magnet for inducing magnetic flux in said material for inspection thereof, in a predetermined inspection position for inspection of said surface, wherein said magnet in said predetermined inspection position induces magnetic flux in said material for inspection and a sensor assembly for detecting magnetic flux leakage from said material indicative of magnetic anomalies in the material, said magnet and said sensor assembly being disposed in a predetermined inspection position with respect to each other and to said surface wherein said magnet is at a first characteristic spacing from said surface and said sensor assembly is in the magnetic field of said magnet at a second characteristic spacing from said surface, said apparatus including a carriage assembly mounted on wheels and sized to permit an operator to maneuver said apparatus at least in part with manual labor over said substantially planar surface for inspection thereof, said apparatus comprising:

means coupled to said carriage assembly for manually steering and manipulating said apparatus;

a mounting assembly movable with respect to said wheels with said magnet and said sensor assembly being mounted thereon;

said mounting assembly having a first position in which said magnet and said sensor assembly are disposed in said predetermined inspection position;

a first actuator mounted on said carriage assembly and coupled to said mounting assembly for moving said mounting assembly between said first position and a retracted position in which said magnet and said sensor assembly are further removed from said surface than said respective first and second characteristic spacings, wherein said magnet in said retracted position provides a reduced magnetic attraction to said surface so as to reduce magnetic resistance to movement of said apparatus on said surface and said sensor assembly in said retracted position provides increased clearance from said surface for avoidance of obstacles; and power means coupled to said first actuator and operable on command from said operator for urging said mounting assembly between said first position and said retracted position, whereby said operator is able to cause said mounting assembly to move to said retracted position for maneuvering said apparatus past obstacles and to return to said first position without disturbing said characteristic spacings for continued inspection of said surface.

2. Magnetic flux leakage inspection apparatus for inspecting a substantially planar surface of a magnetizable material for magnetic anomalies, said apparatus including a magnet for inducing magnetic flux in said material for inspection thereof, and a sensor assembly for detecting magnetic flux leakage from said material indicative of magnetic anomalies in the material, said magnet and said sensor assembly being disposed in a predetermined inspection position wherein said magnet is at a first characteristic spacing from said surface and said sensor assembly is in the magnetic field of said magnet at a second characteristic spacing from said surface, said apparatus including a carriage assembly mounted on wheels and sized to permit an operator to maneuver said apparatus at least in part with manual labor over said substantially planar surface for inspection thereof, said apparatus comprising:

an actuator for moving said magnet between said inspection position and a retracted position further removed from said surface than said first characteristic spacing, wherein said magnet in said retracted position provides a reduced magnetic attraction to said surface so as to reduce magnetic resistance to movement of said apparatus on said surface; and power means coupled to said actuator and operable on command from said operator for urging said magnet between said inspection position and said retracted position, whereby said operator is able to cause said magnet to move to said retracted position for maneuvering said apparatus past obstacles and to return to said inspection position without disturbing said characteristic spacings for continued inspection of said surface;

wherein said magnet in said inspection position is maintained in fixed disposition with respect to said wheels and wherein said apparatus includes a support member having a first end structured for engagement with said surface;

said actuator having a rest position wherein said magnet is in said inspection position and said support member is not in engagement with said surface; and said actuator and said support member being disposed on said carriage assembly such that activation of said actuator when in said rest position brings said first end of said support member into engagement with said surface and urges at least one of said wheels off said surface, thereby urging said magnet to said retracted position.

3. The apparatus of claim 2 wherein said apparatus has forward and rear wheels and said actuator has an extensible actuator rod providing said support member;

said actuator being mounted on said carriage assembly at a position not behind said forward wheels, wherein extension of said actuator rod brings said actuator rod into engagement with said surface and raises said forward wheels off said surface.

4. The apparatus of claim 3 wherein said actuator rod includes a ball castor at said first end for engagement with said surface.

5. The apparatus of claim 1, further comprising:

a second actuator having an extensible actuator rod providing a support member, said actuator rod having a first end structured for engagement with said surface;

said second actuator being mounted on said carriage assembly, wherein extension of said actuator rod brings said first end of said actuator rod into engagement with said surface for support of said apparatus and urges at least one of said wheels off said surface, thereby further retracting said magnet from said surface.

6. A method of maneuvering a magnetic inspection apparatus over a surface of a magnetizable material for inspecting the surface for magnetic anomalies, said apparatus including a magnet for inducing magnetic flux in said material for inspection thereof, and a sensor assembly for detecting magnetic flux leakage from said material indicative of magnetic anomalies in the material, said magnet and said sensor assembly being disposed in a predetermined inspection position with respect to each other and to said surface wherein said magnet is at a first characteristic spacing from said surface and said sensor assembly is in the magnetic field of said magnet at a second characteristic spacing from said surface, said apparatus being mounted on wheels and being sized to permit an operator to maneuver said apparatus at least in part with manual labor over said substantially planar surface for inspection thereof, said method comprising the steps of:

providing an extensible actuator on said apparatus having a first end structured for engagement with said surface;

causing powered extension of said extensible actuator to bring said first end into engagement with said surface and to raise at least one of said wheels off said surface;

maneuvering said apparatus to a desired position and orientation on said surface while said at least one wheel is off said surface; and causing powered retraction of said extensible actuator to bring said at least one wheel into engagement with said surface and to return said magnet to said predetermined inspection position for continued inspection of said surface.

7. A method of maneuvering a magnetic inspection apparatus over a surface of a magnetizable material for inspecting the surface for magnetic anomalies, said apparatus including a magnet for inducing magnetic flux in said material for inspection thereof, and a sensor assembly for detecting magnetic flux leakage from said material indicative of magnetic anomalies in the material, said magnet and said sensor assembly being disposed in a predetermined inspection position with respect to each other and to said surface wherein said magnet is at a first characteristic spacing from said surface and said sensor assembly is in the magnetic field of said magnet at a second characteristic spacing from said surface, said apparatus being mounted on wheels and being sized to permit an operator to maneuver said apparatus at least in part with manual labor over said substantially planar surface for inspection thereof, said method comprising the steps of:

mounting said magnet and said sensor assembly on said inspection apparatus for relative movement with respect to said wheels to and from said surface;

providing a powered actuator coupled to said magnet and to said sensor assembly for moving said magnet and said sensor assembly between said inspection position and a retracted position in which said magnet and said sensor assembly are further removed from said surface than said respective first and second characteristic spacings;

causing powered actuation of said actuator to move said magnet and said sensor assembly to said retracted position when an obstacle is encountered in the path of said inspection apparatus while inspecting said surface;

maneuvering said inspection apparatus over said obstacle; and causing powered retraction of said actuator to return said magnet and said sensor assembly to said predetermined inspection position for continued inspection of said surface.

* * * * *